United States Patent [19]

Noone

[11] Patent Number: 5,746,701
[45] Date of Patent: May 5, 1998

[54] GUIDEWIRE WITH NON-TAPERED TIP

[75] Inventor: Michael S. Noone, Londonderry, N.H.

[73] Assignee: Medtronic, Inc., Minneapolis, Minn.

[21] Appl. No.: 528,035

[22] Filed: Sep. 14, 1995

[51] Int. Cl.⁶ ........................................................ A61B 5/00
[52] U.S. Cl. .............................. 600/585; 604/95; 604/96
[58] Field of Search ............................ 128/772, 657, 128/658; 604/95.6, 280.3

[56] References Cited

U.S. PATENT DOCUMENTS

| | | | |
|---|---|---|---|
| 3,789,841 | 2/1974 | Antoskiw | 128/2.05 R |
| 4,545,390 | 10/1985 | Leary | 128/772 |
| 4,934,380 | 6/1990 | de Toludo | 128/772 |
| 4,998,923 | 3/1991 | Samson et al. | 606/194 |
| 5,095,915 | 3/1992 | Engelson | 128/772 |
| 5,163,445 | 11/1992 | Christian et al. | 128/785 |
| 5,315,996 | 5/1994 | Lundquist | 128/642 |
| 5,404,887 | 4/1995 | Prather | 128/772 |
| 5,406,960 | 4/1995 | Corso, Jr. | 128/772 |
| 5,437,288 | 8/1995 | Schwartz et al. | 128/772 |

FOREIGN PATENT DOCUMENTS

| | | | |
|---|---|---|---|
| 674943 | 8/1990 | Switzerland | 128/772 |
| 9304722 | 3/1993 | WIPO . | |

*Primary Examiner*—Max Hindenburg
*Assistant Examiner*—Pamela L. Wingood
*Attorney, Agent, or Firm*—David S. Brin; Dianne M. F. Plunkett; Harold R. Patton

[57] ABSTRACT

The present invention relates to a guidewire which comprises an elongated core of a substantially solid cross-section having a distal end portion, the distal end portion having a plurality of notches therein, the notches having a depth of 5–25% of the diameter of the proximal end. The proximal end of the guidewire has a diameter in the range of 0.005–0.040 inches, the notches defining a continuous helix with a constant depth. The guidewire also comprises a helically wound spring, the spring having a plurality of coils defining a lumen. At least part of the distal end portion of the elongated core being received within the lumen. That part of the distal end portion of the elongated core being received within the lumen forming with the helically wound spring an intermediate portion, at least a portion of the coils being disposed within the continuous helix of the elongated core, the helically wound spring being sized and positioned on the elongated core such that a smooth continuous outer diameter is attained over the length of the guidewire. The guidewire also has a means for bonding the coils to the distal end portion so that the guidewire has a continuous stiffness gradient along the length of the guidewire from a stiffest point at the proximal end to a more flexible portion in the distal end portion proximal to the intermediate portion, to a still more flexible portion in the intermediate portion to a most flexible point at the distal end of the helically wound spring. In an alternative embodiment the notches define a continuous helix with a constant depth. This alternative embodiment also has a rounded tip connected to the distal end of the spring and a safety wire connecting the distal end portion and the rounded tip.

10 Claims, 12 Drawing Sheets

GUIDEWIRE WITH NON-TAPERED TIP

FIELD OF THE INVENTION

The present invention relates to guidewires, and more particularly, to a guidewire which achieves flexibility in the distal or intermediate portions by virtue of a plurality of notches which are cut into the body or core of the guidewire. Such a guidewire can be used in PTCA procedures such as balloon angioplasty, angiography, atherectomy, stent implantation procedures, or radiology procedures.

BACKGROUND OF THE INVENTION

One of the therapeutic procedures applicable to the present invention is known as percutaneous transluminal coronary angioplasty (PTCA). This procedure can be used, for example, to reduce arterial build-up of cholesterol fats or atherosclerotic plaque. Typically, a guidewire is steered through the vascular system to the lesion site of therapeutic interest. A dilatation catheter is inserted over the guidewire and is tracked along the guidewire to the lesion where the catheter is inflated to dilate the lesion. A guiding catheter acts as a support conduit for both the guidewire and the dilatation catheter.

The considerations in guidewire design include torsional stiffness, or steerability, bending stiffness, or flexibility, tip formability, and radiopacity. In a typical guidewire construction, a tapered stainless steel core wire has a platinum spring coil which is wound around the tapered distal end of the core wire. Spring coil guidewire construction has been known in the art for many years. An early example of guidewire construction includes U.S. Pat. No. 3,789,841, issued to Antoshkiw.

U.S. Pat. No. 5,315,996, issued to Lundquist, discloses a catheter comprising a flexible elongate tubular shaft. The shaft is comprised of a torque tube which has a cylindrical wall with at least one flexible portion therein with the flexible portion being characterized in that at least one slot is provided in the cylindrical wall. A flexible sleeve encloses the torque tube.

U.S. Pat. No. 5,095,915, issued to Engelson, discloses a catheter guidewire composed of a wire core whose distal end section is encased in a polymer sleeve. Axially spaced grooves formed in the sleeve increase the flexibility of the core end section.

U.S. Pat. No. 4,998,923, issued to Samson, discloses a steerable dilatation catheter which comprises an elongated tubular member which is longitudinally relatively flexible but diametrically relatively rigid. The elongated tubular member is preferably a hypotube of stainless steel or nitinol.

U.S. Pat. No. 4,545,390, issued to Leary, discloses a guidewire with a major portion which is a small diameter flexible rod. The distal region of the rod is tapered. The tapered portion is surrounded by a helically wound spring.

SUMMARY OF THE INVENTION

It is an object of the invention to provide a guidewire which achieves differential flexural stiffness to allow sufficient flexibility in the distal end for positioning the distal end within the coronary vasculature while allowing for sufficient columnar strength in the proximal region to facilitate moving the guidewire through the tortuous illio-femoral vasculature of the patient. Further, the guidewire must possess the requisite torsional stiffness to facilitate the positioning and rotation of the guidewire within the vasculature.

In accordance with the object of the invention, the present invention relates to a guidewire which comprises an elongated core, the distal end portion of which has been made more flexible by cutting notches 2–25% of the diameter into the elongated core. The notches may be a continuous helical notch or discrete, axially or circumferentially spaced notches in the distal end portion. A guidewire so constructed has the advantage of being of unitary construction while allowing for flexural stiffness in the distal end portion, columnar strength in the proximal region, and torsional stiffness along the length of the guidewire.

In an alternative embodiment, the distal end portion of the elongated core may be ground to a constant diameter which is smaller than that of the proximal end of the elongated core. In an additional embodiment, the distal end portion may be ground to a diameter which tapers from a larger diameter adjacent to the proximal end to a smaller diameter at the distal end of the distal end portion. In both such embodiments, the distal end portion is also notched to further increase flexibility.

In an alternative embodiment, a polymeric sleeve may be bonded to the distal end portion of the elongated core to encase the notched distal end portion, thus allowing for the facile and lubricious movement of the distal end portion through the vasculature and to prevent the creation of thrombus between the notches.

In an additional embodiment, a helically wound spring is disposed at its proximal end within a continuous helical notch in the distal end portion of the elongated core. The spring is then bonded to the elongated core using a suitable means. The distal end of the spring extends distally of the distal end portion of the elongated core, and a rounded tip is attached to the distal end of the spring to reduce trauma to the vasculature. A safety wire is connected at one end to the distal end portion of the elongated core and at the other end to the rounded tip. The distal end portion of the elongated core may also be either ground to a smaller diameter or to a taper relative to the diameter of the proximal end, as described previously.

In an alternative embodiment, the elongated core is notched in an intermediate portion and is either tapered or is made of a smaller diameter in the distal end portion. A helically wound spring is disposed at its proximal end within a continuous helical notch in the intermediate portion. The distal end of the spring extends distally of the distal end portion of the elongated core, as discussed previously.

DETAILED DESCRIPTION OF THE PREFERRED EMBODIMENTS

Applicants' guidewire comprises a unitary construction of an elongated core of a solid circular cross-section of a preferred diameter of 0.014 inches. Alternative diameters which are suitable for the invention are in the range of 0.005 to 0.040 inches. The 0.040 inch diameter is typically used in angiography applications, where a substantially rigid guidewire is required to introduce an angiography catheter into the vasculature. The overall length of the guidewire is preferably 175 cm, or optionally, 300 cm. The 175 cm length affords the physician with sufficient working length outside of the patient for manipulation of the guidewire within the patient vasculature. The 300 cm length guidewire is used to exchange a first dilatation catheter for a second dilatation catheter without the necessity of removing the guidewire from the vasculature. The guidewire is preferably constructed of a stainless steel, preferably a 300 series which has been annealed to allow for adequate elasticity without kinking or buckling. Alternative materials include the class of nickel titanium alloys known as NITINOL, which exhibit superelastic behavior relative to stainless steels and are thus more kink and buckle resistant than stainless steel. Preferred NITINOL compositions include 49% to 51% atomic percent of elemental Nickel, such as that obtainable from the Raychem Corporation. The guidewire includes a proximal end and a distal end portion. The distal end portion is preferably 32 cm in length. The preferred length is based upon the typical length between the target lesion and the apex of the aortic arch of the patient so that adequate flexibility is achieved in the distal end portion to position the guidewire in the lesion. Optionally, if more support is required of the guidewire, such as when employing a therapeutic device with a large crosssectional diameter, such as an atherectomy device, the length of the distal end portion is in the range of 5 to 10 cm. Additionally, if the vasculature is unusually tortuous, requiring greater flexibility of the guidewire, the length of the distal end portion is in the range of 50 cm, which allows for flexibility in the often tortuous illio-femoral region of the anatomy.

Figure 1:
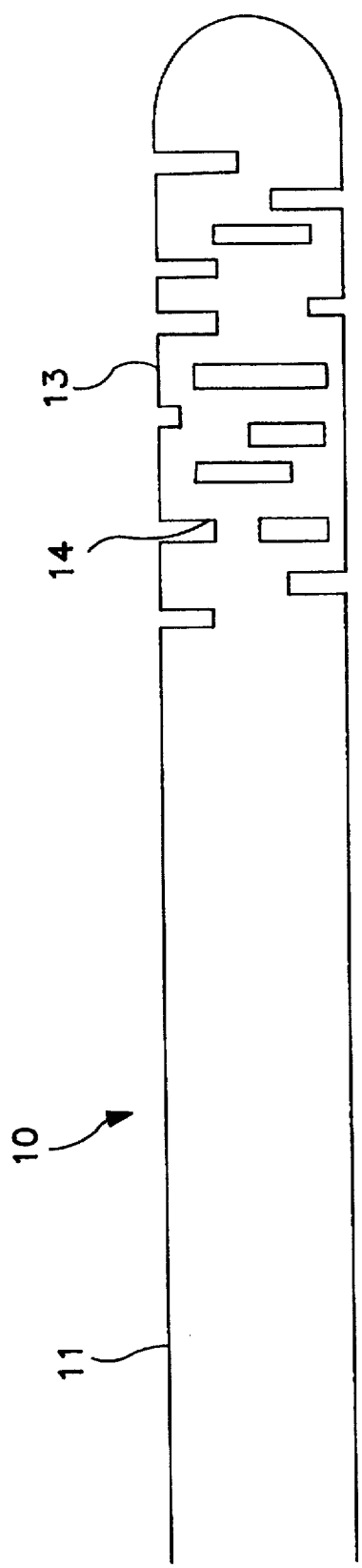
FIG. 1 depicts applicants' first embodiment of a unitary guidewire construction with a notched distal end portion.

In the distal end portion 13 of the guidewire 10 in FIG. 1, a plurality of notches 14 are cut. The notches 14 are preferably axially spaced, circumferential notches of width 0.010, of depth 0.004 and an axial spacing of 0.025 inches. The notches 14 are cut with conventional laser cutting equipment, or alternatively, a high speed diamond wheel grinder. Alternatively, the notches 14 may be discrete and non-circumferential and varying in depth along the length of the distal end portion 13. In this manner, the flexibility of the guidewire 10 may be varied in a step-wise fashion over the length of the distal end portion 13. The cross-section of the guidewire 10 is preferably solid, as opposed to annular. Annular cross-sections which are then "slotted" for flexibility are common to the prior art. The solid cross-section affords greater flexural stability against buckling or kinking of the guidewire 10 than an annular cross-section because of the moment of inertia of the solid section as compared to an annular section. *Mark's Standard Handbook for Mechanical Engineers*, 9th Edition (McGraw-Hill, 1986) defines flexural stress as being inversely proportional to the moment of inertia of the cross-section. For a solid cross-section with a diameter, D, the moment of inertia, I, is defined as:

$$I = 1/64 * (D^4).$$

The moment of inertia for an annular cross-section of outer diameter, D, and inner diameter, d, is defined as:

$$I = 1/64 * (D^4 - d^4).$$

Because, for the same diameter, D, for a solid cross-section and an annular cross-section, the moment of inertia for a solid cross-section is higher than the annular cross-section, the flexural stress of a solid cross-section is less than that of an annular cross-section where an equivalent bending moment is applied. Consequently, the solid cross-section can withstand a larger bending moment than the annular cross-section, thus yielding a more buckle-resistant or kink-resistant guidewire.

Figure 2:
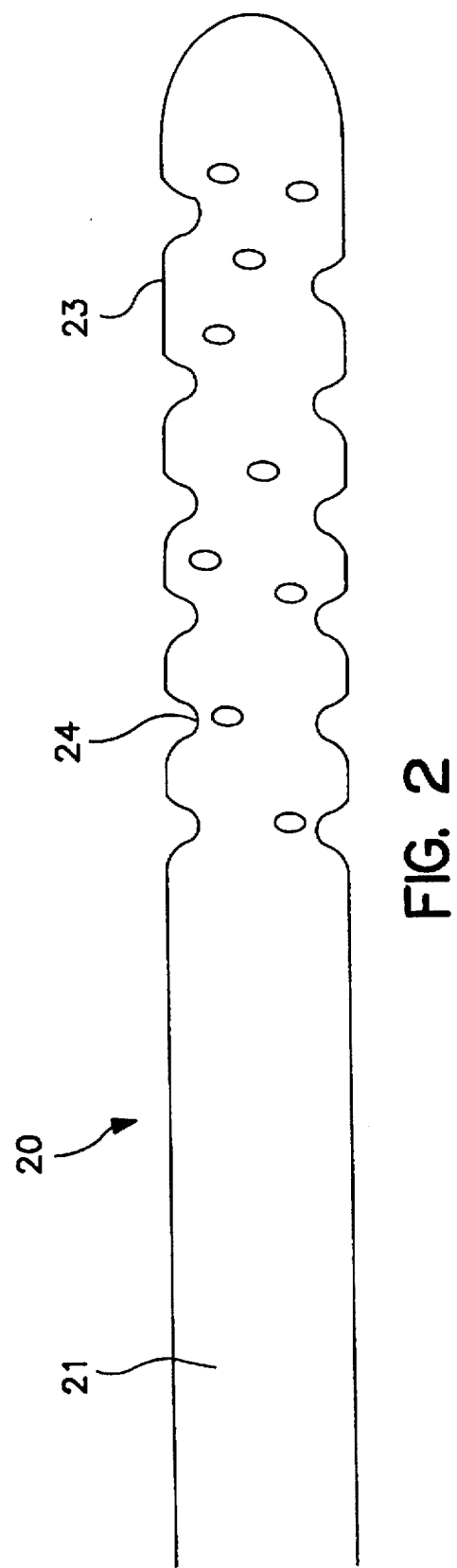
FIG. 2 depicts applicants' guidewire with smoothly radiused notches.

Referring to FIG. 2, guidewire 20 is depicted where the notches 24 are shown in a shape which characterizes a low stress concentration factor because of the smooth radii which comprise the notches 24. By employing the notches 24 in FIG. 2, the low stress concentration factor created at the interior region of the notch 24 improves the resiliency and resistance to kinking and buckling of the distal end portion 23. Preferably, the depth of the notches is approximately 20% of the diameter of the proximal end 21. With such a depth, the guidewire 20 in the region of the notches 24 is approximately 50% less stiff than the proximal end 21. The depth of the notches 24 may be varied along the length of the distal end portion 23 so that variable stiffness is achieved in the guidewire 20. Alternatively, with the notches 24 of a depth of 5% of the diameter of the proximal end 21, the distal end portion 23 is approximately 20% less stiff than the proximal end 21.

Figure 3:
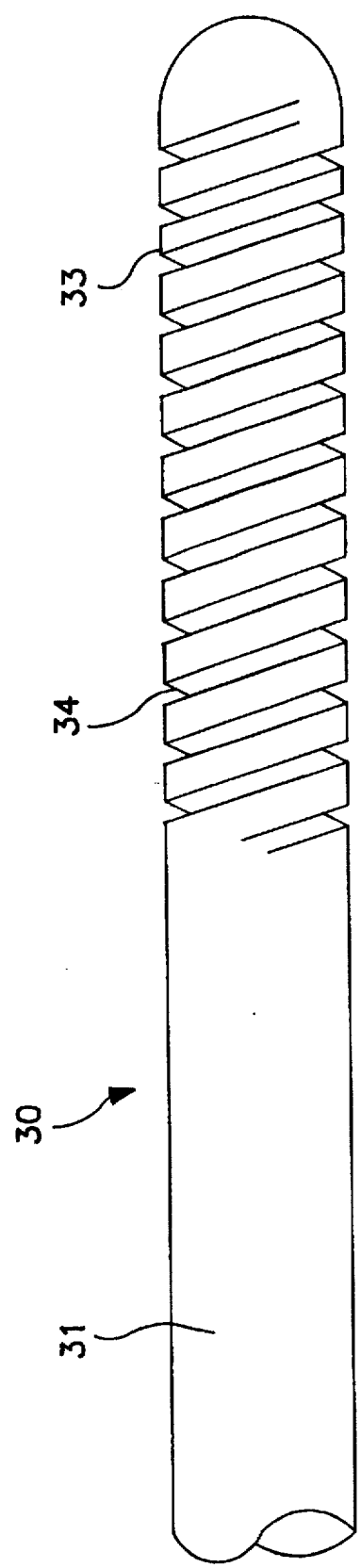
FIG. 3 depicts applicants' guidewire with notches which define a continuous helix.

Referring to the guidewire 30 in FIG. 3, the notches 34 are shown as a continuous helix over the length of the distal end portion 33. The continuous helix is preferably of a width of 0.010, a depth of 0.002, and a pitch of 0.025 inches and begins at the distal end of the proximal section 31.

Figure 4:
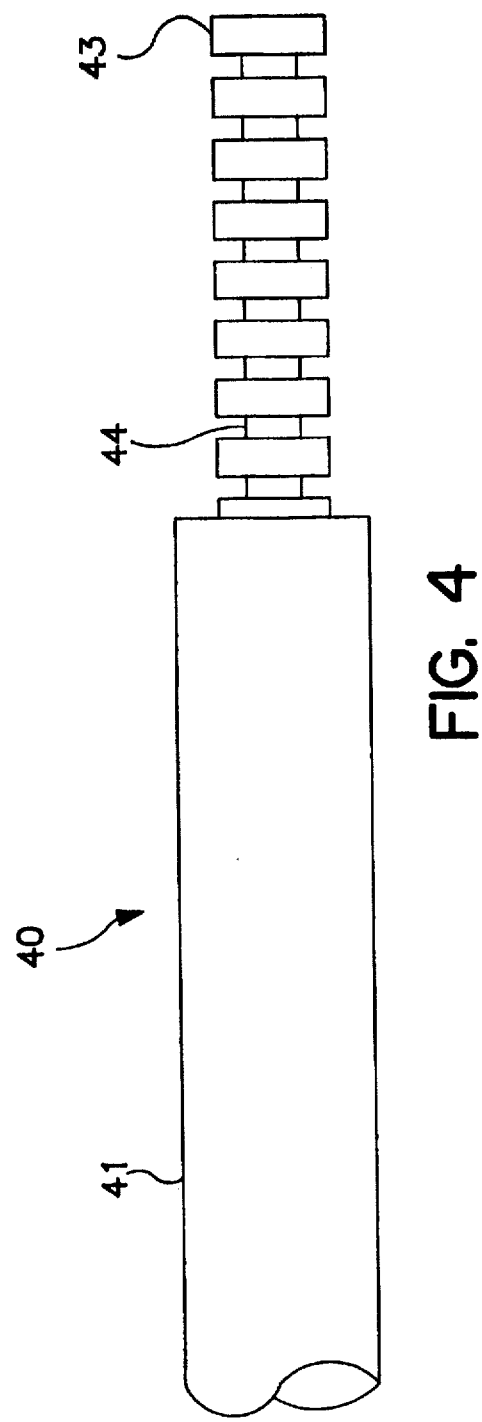
FIG. 4 depicts applicants' guidewire with a smaller diameter distally than proximally and with axially spaced circumferential notches.

Referring to FIG. 4, an additional embodiment of a guidewire 40 is shown which depicts a distal end portion 43 which is smaller than the proximal end 41 of the guidewire 40 and which has a plurality of notches 44 cut in the distal end portion 43. The diameter of the proximal end 41 is preferably 0.014 inches while the diameter of the distal end portion 43 is preferably 0.010 inches. The notches 44 are preferably axially spaced, circumferential notches of width 0.010, of depth 0.002, and an axial spacing of 0.025 inches.

Figure 5:
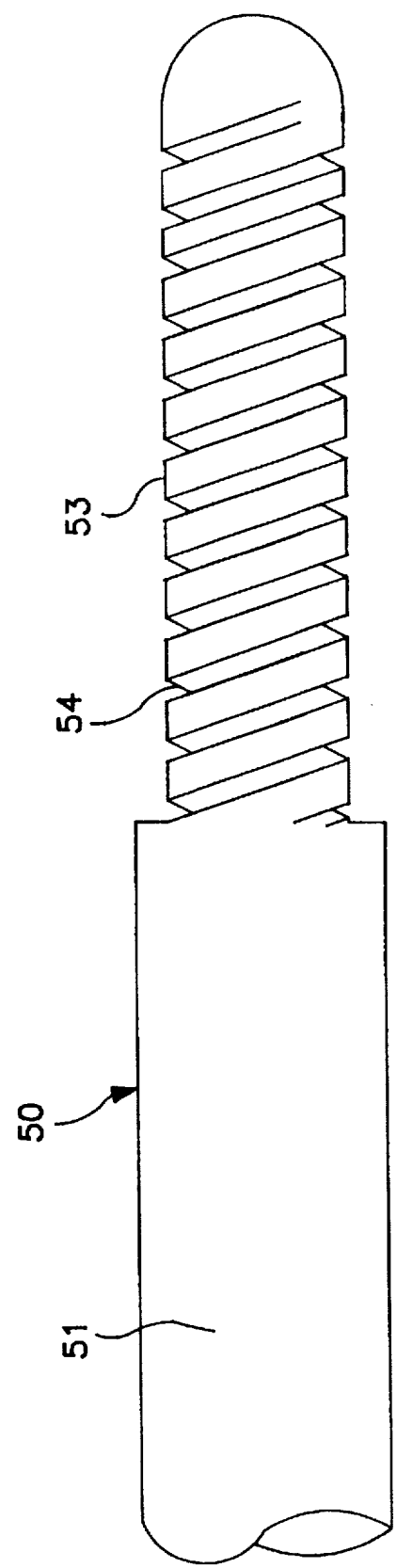
FIG. 5 depicts applicants' guidewire with a smaller diameter distally than proximally and with notches which define a continuous helix.

Alternatively, the notches 54 may be a continuous helix over the length of the distal end portion 53 of the guidewire 50, as shown in FIG. 5. The continuous helix begins at the distal end of the proximal section 51 and has preferably of a width of 0.010, a depth of 0.002 and a pitch of 0.025 inches. Preferably, the distal end portion 53 tapers from a diameter of 0.014 inches at a point adjacent to the proximal end 51 to a diameter of 0.010 inches at the distal end of the distal end portion 53.

Figure 6:
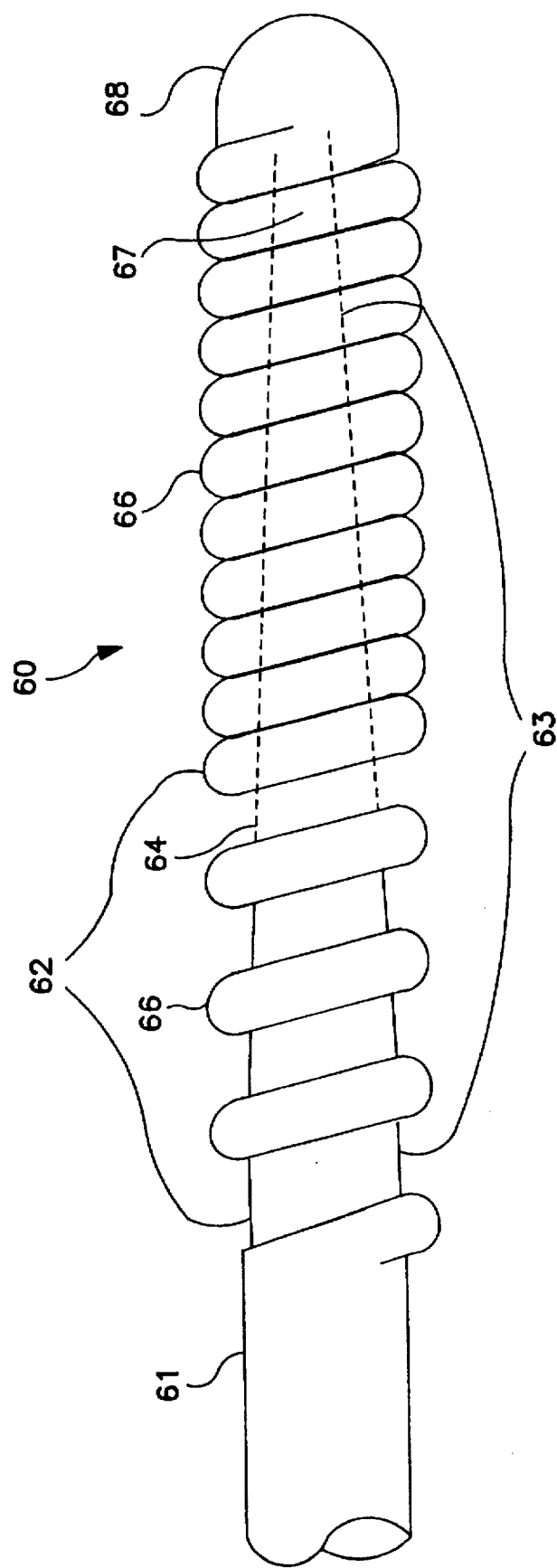
FIG. 6 depicts applicants' guidewire with an intermediate portion which is notched, a distal end portion which is tapered, and with a helically wound spring disposed over and connected to the intermediate and distal end portions.

Referring to FIG. 6, the guidewire 60 has an intermediate region 62 which has notches 64 which define a continuous helix and a distal end portion 63 which tapers from a larger diameter adjacent to the proximal end 61, to a smaller diameter distally of the distal end portion 63. The helix is of a 0.010 inch width and a 0.025 inch pitch over the length of the distal end portion 63. Preferably, the distal end portion 63 tapers from a diameter of 0.014 inches at a point adjacent to the proximal end 61 to a diameter of 0.008 inches at the distal end of the distal end portion 63. A helically wound spring 66, is disposed over the intermediate portion 62 and the distal end portion 63. At the proximal end of the helically wound spring 66, the coils of the helically wound spring 66 are separated to a preferred pitch of 0.025 inches and placed within the notches 64 in the intermediate portion 62. Preferably, the helically wound spring 66 comprises a 300 series stainless steel which has been annealed with a wire diameter of 0.0035 inches. The coils of the helically wound spring 66 are then bonded to the intermediate portion 62 using a means for bonding such as soldering, brazing, welding, or adhesive bonding. A portion of the helically wound spring 66 extends distally of the distal end portion 63 so that the guidewire 60 has a continuous stiffness gradient along the length of the guidewire 60 from its stiffest point at the proximal end 61 to a more flexible point in the intermediate portion 62, by virtue of the notches 64 and the proximal end of the helically wound spring 66, to a further more flexible point along the distal end portion 63. The most flexible point of the guidewire 60 is at the distal end of the helically wound spring 66. A safety wire 67 is connected between the distal end portion 63 and the distal end of the helically wound spring 66 to give the connection between the distal end portion 63 and the helically wound spring 66 an additional measure of safety yet not a sustantial increase in stiffness. The safety wire 67, preferably a stainless steel of 0.004 inches diameter, is soldered, brazed, or welded to the distal end portion 63 and to the distal end of the helically wound spring 66. Connected to the distal end of the helically wound spring 66 is a rounded tip 68, which comprises a bead of solder, braze, or weld which is ground or sanded to produce a rounded tip 68.

Figure 7:
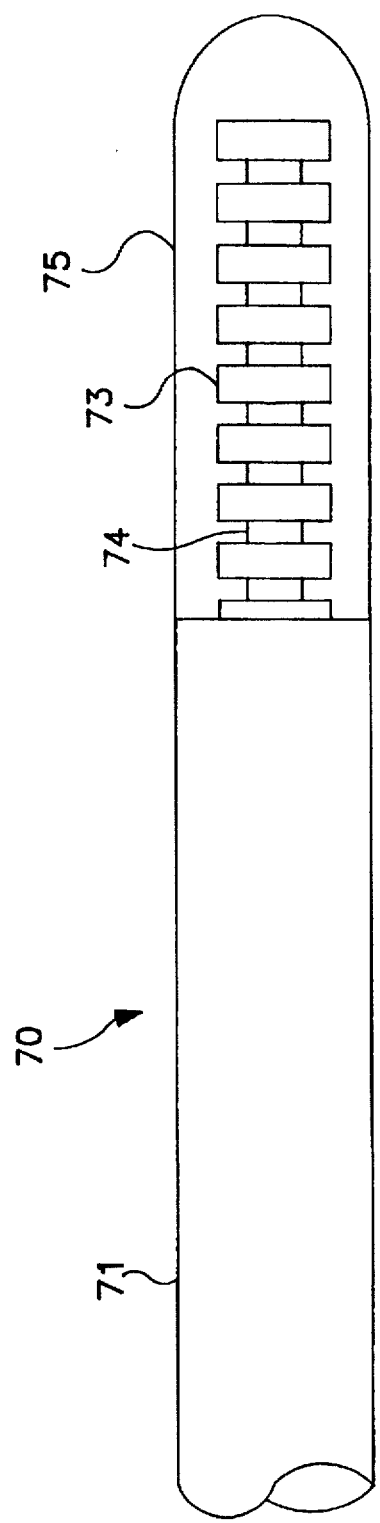
FIG. 7 depicts applicants' guidewire with a smaller diameter distally than proximally with axially spaced circumferential notches and with a polymer sleeve disposed over the distal end portion.

Referring to FIG. 7, an embodiment is shown which depicts a polymeric sleeve 75, which is placed over the distal end portion 73. The polymeric sleeve 75 may be comprised of either a polyurethane, a nylon, or a fluoropolymer. Preferably, the polymeric sleeve 75 is comprised of a fluoropolymer such as TEFLON®, obtainable from the E.I. DuPont de Nemours and Company, Wilmington, Del. The diameter of the proximal end 71 is preferably 0.014 inches while the diameter of the distal end portion 73 is preferably 0.010 inches. The notches 74 in the distal end portion 73 are preferably axially spaced, circumferential notches of width 0.010, of depth 0.002, and an axial spacing of 0.025 inches. The polymeric sleeve 75 is a heat-shrinkable TEFLON® which has a recovered inside diameter of 0.012 inches and a recovered wall thickness of 0.002 inches. The polymeric sleeve 75 is abutted against the transition between the proximal end 71 and the distal end portion 73 so that a smooth continuous outer diameter of 0.014 inches is obtained over the length of the guidewire 70.

Figure 8:
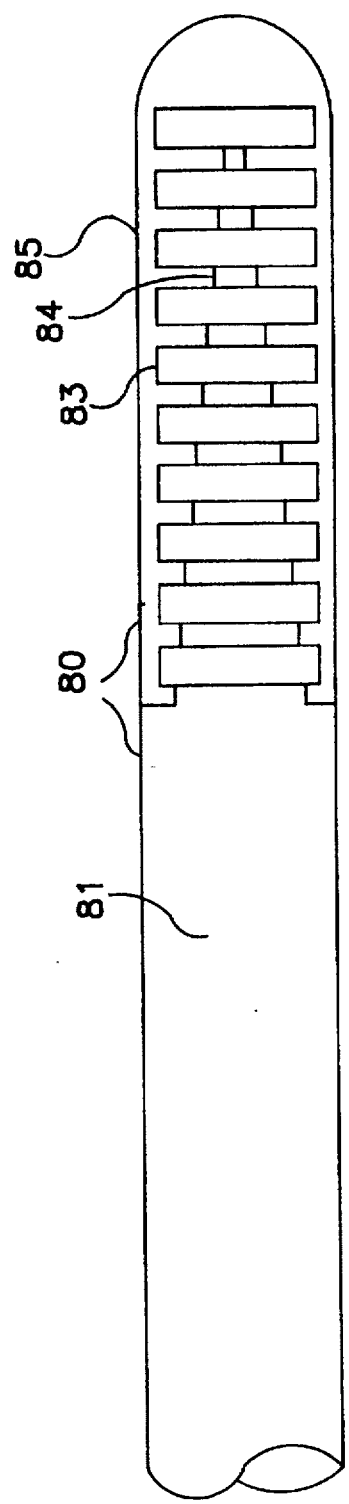
FIG. 8 depicts applicants' guidewire with a tapered diameter, axially spaced circumferential notches and with a polymer sleeve disposed over the distal end portion.

Referring to FIG. 8, a polymeric sleeve 85 is disposed over a tapered distal end portion 83. The distal end portion 83 tapers from a larger diameter adjacent to the proximal end 81, to a smaller diameter distally. Preferably, the distal end portion 83 tapers from a diameter of 0.014 inches at a point adjacent to the proximal end 81 to a diameter of 0.010 inches at the distal end of the distal end portion 83. Because of the tapered profile of the distal end portion 83, the profile of the inner surface of the polymeric sleeve 85 is preferably tapered to mate with the profile of the distal end portion 83. With a preferred taper of 0.02% based upon a preferred length of the distal end portion 83 of 32 cm, the polymeric sleeve is preferably insert molded over the distal end portion 83. Materials suitable for insert molding include polyurethanes and nylons, and preferably a polyether block amide such as PEBAXS®, obtainable from the Elf Ato-Chem Corporation, Philadelphia, PA. In the insert molding process, the injected PEBAXO® fills the notches 84 in the distal end portion 83. The polymeric sleeve 85 is positioned relative to the proximal end of the distal end portion 83 so that a smooth continuous diameter is attained over the length of the guidewire 80. The notches 84 are preferably axially spaced, circumferential notches of width 0.010, of depth 0.002, and an axial spacing of 0.025 inches. Because of the PEBAX ® material shrinkage upon cooling, the polymeric sleeve 85 is bonded to the distal end portion 83. The distal end of the polymeric sleeve 85 can then be radiused using a fine grit sandpaper to produce a rounded distal tip profile for the polymeric sleeve 85.

Figure 9:
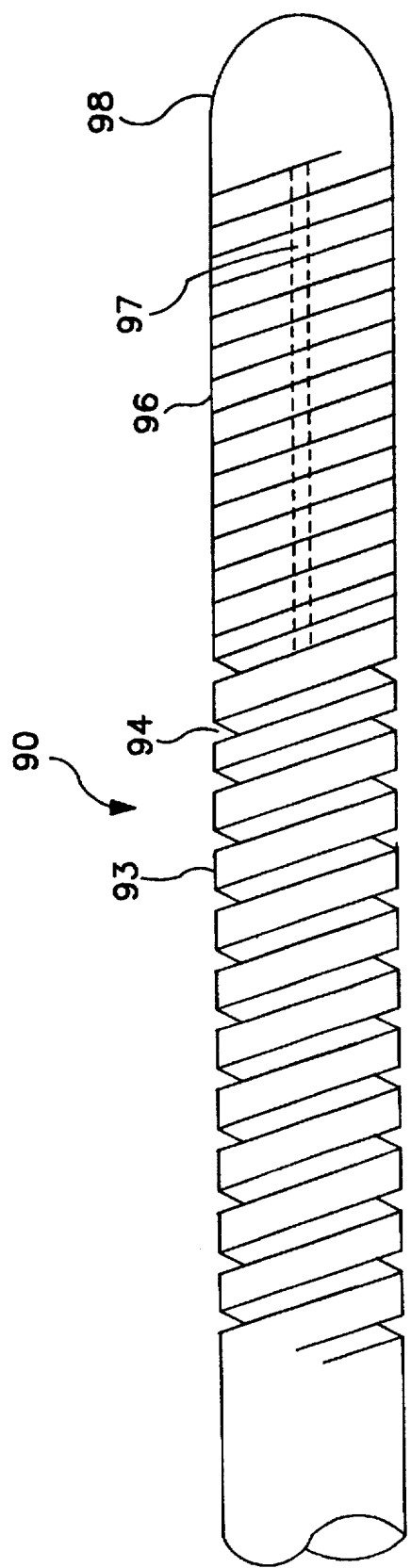
FIG. 9 depicts applicants' guidewire with a notched distal end portion which defines a continuous helix and a helically wound spring disposed over and connected to the distal end portion.

Referring to FIG. 9, an embodiment of a guidewire 90 is shown where the notches 94 in the distal end portion 93 define a continuous helix. The continuous helix is preferably of a width of 0.010, a depth of 0.004and a pitch of 0.025 inches. A helically wound spring 96, is disposed over the distal end portion 93. At the proximal end of the helically wound spring 96, the coils of the helically wound spring 96 are separated to a preferred pitch of 0.025 inches and placed within the notches 94 in the distal end portion 93. The coils of the helically wound spring 96 are then bonded to the distal end portion 93 using a means for bonding such as soldering, brazing, welding, or adhesive bonding. Preferably, the helically wound spring 96 comprises a 300 series stainless steel which has been annealed with a wire diameter of 0.0035 inches. The distal end of the helically wound spring 96 extends distally of the distal end portion 93. Preferably, the distal end portion 93 has a length of 32 cm and the helically wound spring 96 extends distally of the distal end portion 93 by 2 cm. Alternatively, a radio-dense material such as tantalum, tungsten, or platinum may be used for the helically wound spring 96. A safety wire 97 is connected between the distal end portion 93 and the distal end of the helically wound spring 96 to give the connection between the distal end portion 93 and the helically wound spring 96 an additional measure of safety. The safety wire 97, preferably a stainless steel of 0.004 inches diameter, is soldered, brazed, or welded to the distal end portion 93 and to the distal end of the helically wound spring 96. Connected to the distal end of the helically wound spring 96 is a rounded tip 98, which comprises a bead of solder, braze, or weld which is ground or sanded to produce a rounded tip 98.

Figure 10:
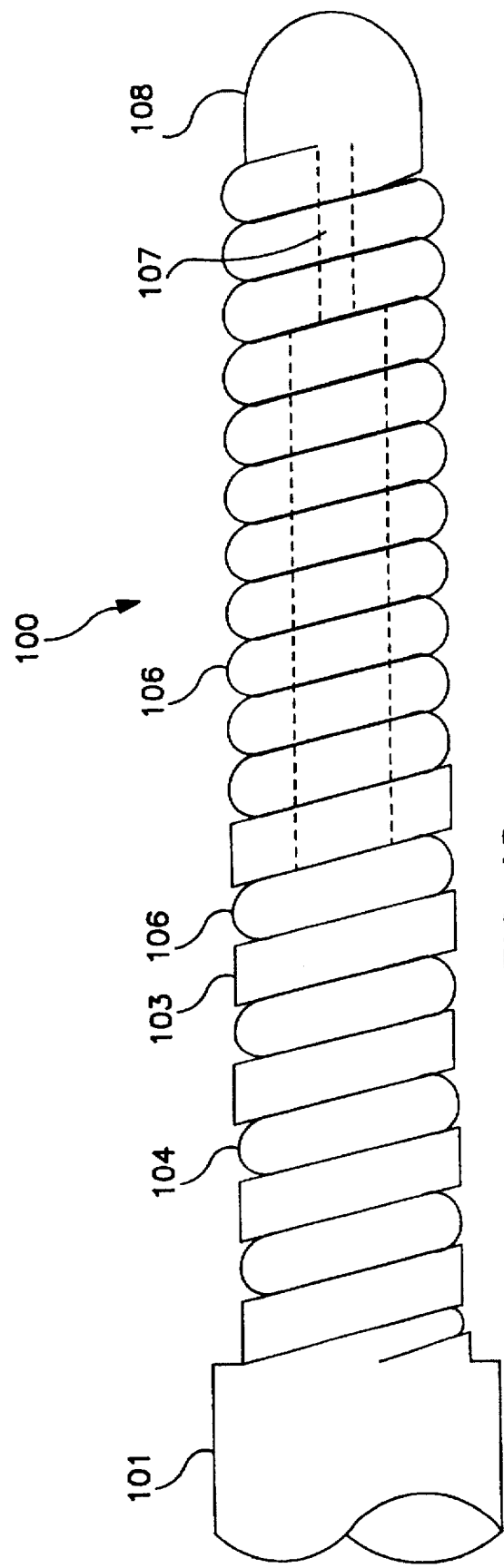
FIG. 10 depicts applicants' guidewire with a distal end portion which is notched to a continuous helix and of a smaller diameter than the proximal end of the guidewire and with a helically wound spring disposed over and connected to the distal end portion.

Referring to FIG. 10, a guidewire 100 is shown with a distal end portion 103 which is smaller than the proximal end 101 of the guidewire 100 and in which the notches 104 are a continuous helix over the length of the distal end portion 103. The continuous helix is preferably of a width of 0.010, a depth of 0.002, and a pitch of 0.025 inches. The diameter of the proximal end 101 is preferably 0.014 inches while the diameter of the distal end portion 103 is preferably 0.010. inches. A helically wound spring 106, is disposed over the distal end portion 103. At the proximal end of the helically wound spring 106, the coils of the helically wound spring 106 are separated to a preferred pitch of 0.025 inches and placed within the notches 104 in the distal end portion 103. The coils of the helically wound spring 106 are then bonded to the distal end portion 103 using means previously described. A safety wire 107 and a rounded tip 108 complete the assembly, as previously described.

Figure 11:
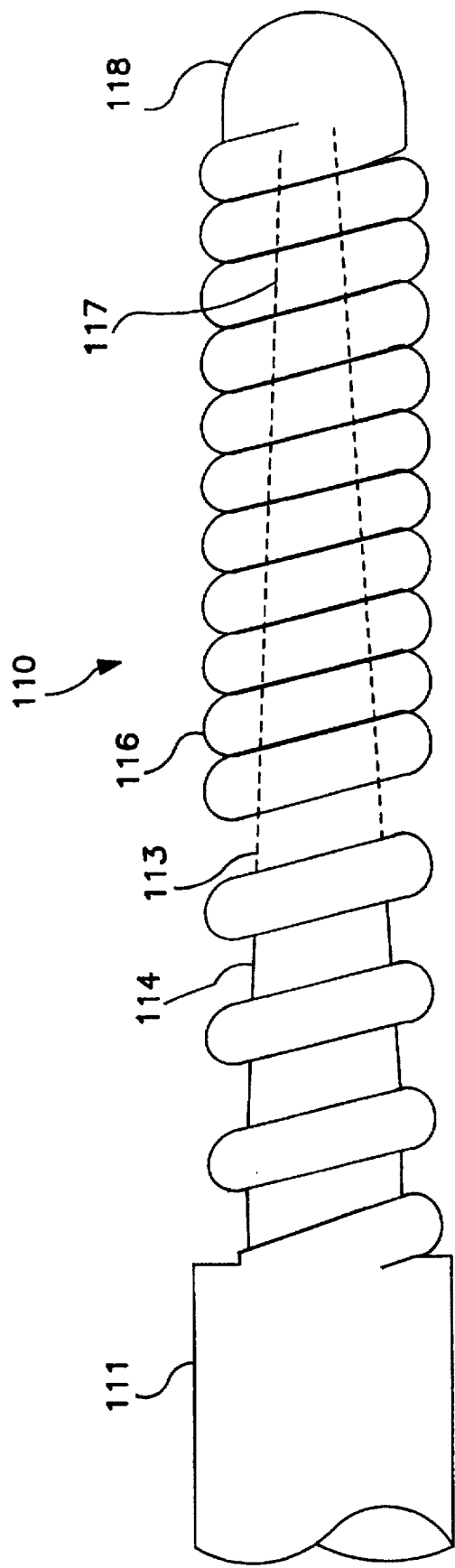
FIG. 11 depicts applicants' guidewire with a distal end portion which is notched to a continuous helix and tapered relative to the proximal end of the guidewire and with a helically wound spring disposed over and connected to the distal end portion.

Referring to FIG. 11, a guidewire 110 is shown with a distal end portion 113 which tapers from a larger diameter adjacent to the proximal end 111, to a smaller diameter distally and in which the notches 114 are a continuous helix over the length of the distal end portion 113. Preferably, the distal end portion 113 tapers from a diameter of 0.014 inches at a point adjacent to the proximal end 111 to a diameter of 0.010 inches at the distal end of the distal end portion 113. The helix is of a 0.010 inch width and a 0.025 inch pitch over the length of the distal end portion 113. The depth of the helix tapers from 0.004 inches at a point adjacent to the proximal end 111 to 0.002 inches at the distal end of the distal end portion 113. A helically wound spring 116, is disposed over the distal end portion 113. At the proximal end of the helically wound spring 116, the coils of the helically wound spring 116 are separated to a preferred pitch of 0.025 inches and placed within the notches 114 in the distal end portion 113. The coils of the helically wound spring 116 are then bonded to the distal end portion 113 using means previously described. A safety wire 117 and a rounded tip 118 complete the assembly, as previously described.

Figure 12:
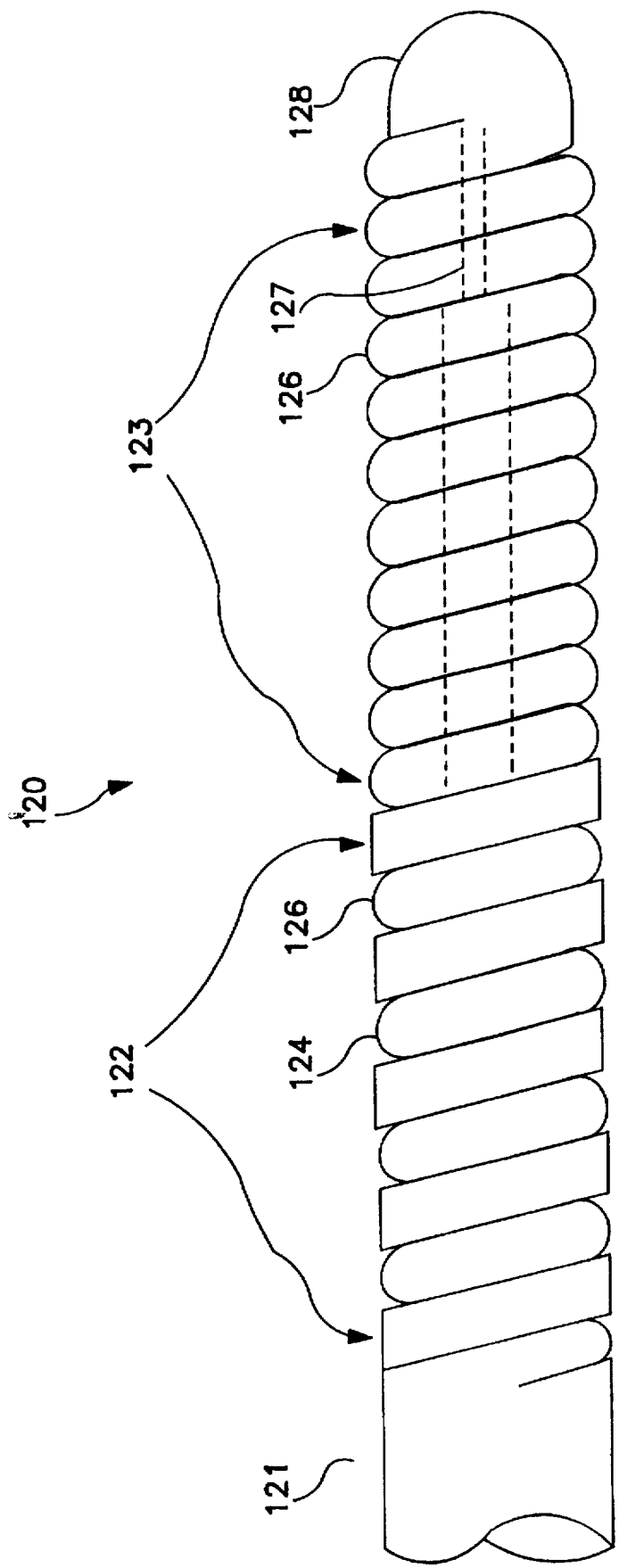
FIG. 12 depicts applicants' guidewire with an intermediate portion which is notched, a distal end portion which is of a smaller diameter than that of the proximal end, and with a helically wound spring disposed over and connected to the intermediate and distal end portions.

Referring to FIG. 12, the guidewire 120 has an intermediate region 122 which has notches 124 which define a continuous helix. The continuous helix is preferably of a width of 0.010, a depth of 0.004and a pitch of 0.025 inches. The diameter of the distal end portion 123 is smaller than that of the proximal end 121. The diameter of the proximal end 121 is preferably 0.014 inches while the diameter of the distal end portion 123 is preferably 0.008 inches. A helically wound spring 126, is disposed over the intermediate portion 122 and the distal end portion 123. At the proximal end of the helically wound spring 126, the coils of the helically wound spring 126 are separated to a preferred pitch of 0.025 inches and placed within the notches 124 in the intermediate portion 122. The coils of the helically wound spring 126 are then bonded to the intermediate portion 122 using means discussed previously. A safety wire 127 and a rounded tip 128 complete the assembly, as previously described.

The preceding embodiments are illustrative of the invention and modifications may be made to these embodiments without departing from the scope and breadth of the invention.

What is claimed is:

1. A guidewire comprising:
   an elongated core of a substantially solid cross-section having a proximal end and a distal end portion, the distal end portion having a plurality of notches therein, the notches having a depth of 5–25% of the diameter of the proximal end, the proximal end having a diameter in the range of 0.005–0.040 inches, the notches defining a continuous helix with a constant depth;
   a helically wound spring, the spring having a proximal end, a distal end, a plurality of coils, and defining a lumen, at least part of the distal end portion of the elongated core being received within the lumen, the part of the distal end portion of the elongated core being received within the lumen forming with the helically wound spring an intermediate portion, at least a portion of the coils being disposed within the continuous helix of the elongated core, the helically wound spring being sized and positioned on the elongated core such that a smooth continuous outer diameter is attained over the length of the guidewire, and
   means for bonding the coils to the distal end portion,
   so that the guidewire has a continuous stiffness gradient along the length of the guidewire from a stiffest point at the proximal end to a more flexible portion in the distal end portion proximal to the intermediate portion, to a still more flexible portion in the intermediate portion to a most flexible point at the distal end of the helically wound spring.

2. The guidewire according to claim 1, further comprising:
   a) a rounded tip, connected to the distal end of the spring; and
   b) a safety wire, the safety wire having a first end and a second end, the first end being connected to the distal end portion, the second end being connected to the rounded tip.

3. The guidewire according to claim 1 wherein the elongated core is selected from the group consisting of stainless steel and nickel titanium alloys.

4. The guidewire according to claim 1 wherein the distal end portion tapers from a larger diameter adjacent to the proximal end to a smaller diameter distally.

5. The guidewire according to claim 1 wherein the distal end portion is a straight taper from the proximal end of the distal end portion to the distal end.

6. The guidewire according to claim 1 wherein the distal end portion is a smaller diameter than the proximal end.

7. The guidewire according to claim 1 wherein the distal end portion is smaller in diameter than the proximal end and tapers from a larger diameter adjacent to the proximal end to a smaller diameter distally.

8. The guidewire according to claim 1 wherein the distal end of the distal end portion is smaller in diameter than the portion of the coils being disposed within the continuous helix of the elongated core.

9. A guidewire comprising:
   an elongated core of a substantially solid cross-section having a proximal end and a distal end portion, the distal end portion having a plurality of notches therein, the notches having a depth of 5–25% of the diameter of the proximal end, the proximal end having a diameter in the range of 0.005–0.040 inches, the notches defining a continuous helix with a constant depth;
   a helically wound spring, the spring having a proximal end, a distal end, a plurality of coils, and defining a lumen, at least part of the distal end portion of the elongated core being received within the lumen, the part of the distal end portion of the elongated core being received within the lumen forming with the helically wound spring an intermediate portion, at least a portion of the coils being disposed within the continuous helix of the elongated core, the helically wound spring being sized and positioned on the elongated core such that a smooth continuous outer diameter is attained over the length of the guidewire;
   means for bonding the coils to the distal end portion;
   a rounded tip, connected to the distal end of the spring; and
   a safety wire, the safety wire having a first end and a second end, the first end being connected to the distal end portion, the second end being connected to the rounded tip;

so that the guidewire has a continuous stiffness gradient along the length of the guidewire from a stiffest point at the proximal end to a more flexible portion in the distal end portion proximal to the intermediate portion, to a still more flexible portion in the intermediate portion to a most flexible point at the distal end of the helically wound spring.

10. The guidewire according to claim 9 wherein the elongated core is selected from the group consisting of stainless steel and nickel titanium alloys.

* * * * *